US00PP33017P3

(12) United States Plant Patent
Probasco et al.

(10) Patent No.: US PP33,017 P3
(45) Date of Patent: May 4, 2021

(54) HOP PLANT NAMED 'HBC 637'

(50) Latin Name: *Humulus lupulus*
Varietal Denomination: HBC 637

(71) Applicant: HOP BREEDING COMPANY, L.L.C., Yakima, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 16/602,650

(22) Filed: Nov. 14, 2019

(65) Prior Publication Data

US 2020/0163267 P1 May 21, 2020

Related U.S. Application Data

(60) Provisional application No. 62/917,008, filed on Nov. 14, 2018.

(51) Int. Cl.
*A01H 5/02* (2018.01)
*A01H 6/00* (2018.01)
*A01H 6/28* (2018.01)

(52) U.S. Cl.
USPC ..... Plt./236
CPC ..... *A01H 6/00* (2018.05); *A01H 5/02* (2013.01); *A01H 6/28* (2018.05)

(58) Field of Classification Search
USPC ..... Plt./236
CPC ..... A01H 6/28
See application file for complete search history.

*Primary Examiner* — Anne Marie Grunberg
(74) *Attorney, Agent, or Firm* — Svendsen Legal, LLC

(57) ABSTRACT

A new hop plant named 'HBC 637' is disclosed. 'HBC 637' is used for its exceptional and unique aromatic qualities, and is suitable for beer flavoring.

3 Drawing Sheets

Genus and species: *Humulus lupulus*.
Variety denomination: 'HBC 637'.

STATEMENT REGARDING FEDERALLY SPONSORED RESEARCH OR DEVELOPMENT

None

BACKGROUND OF THE INVENTION

'HBC 637' is a product of a controlled breeding program carried out by the inventors in the Yakima Valley of Washington State. 'HBC 637' was one of several seedlings resulting from a controlled cross made in 2008 with female parent 'HBC 366' (U.S. Plant Pat. No. 25,899) and male parent '21-10-21' (unpatented). Seedlings from this cross were planted in 2009, and screened for disease and sex in a greenhouse and field nursery near Toppenish, Wash. A single plant of 'HBC 637' was selected in 2011, and in 2012 was expanded to two, seven-hill plots, which were planted near Toppenish, Wash. The plants were observed and evaluated for several years, and in 2018 'HBC 637' was further expanded by asexual tissue culture propagation which occurred near Toppenish, Wash., and then transferred to a 1 acre test plot near Toppenish, Wash. Throughout several generations of asexual propagation, 'HBC 637' has been observed to retain its distinctive characteristics and remain true to type.

BRIEF DESCRIPTION OF THE PHOTOGRAPHS

Figure 1:
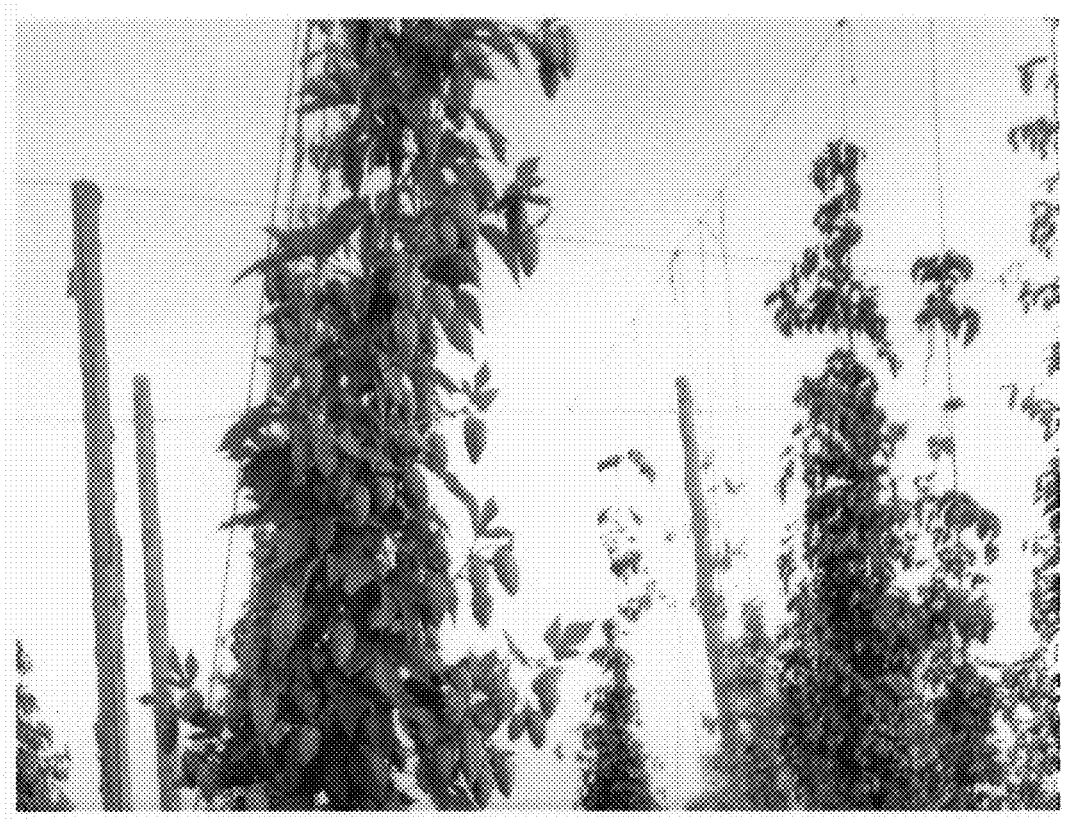
FIG. 1 illustrates a mature 'HBC 637' hop plant as grown on a trellis.
Figure 2:
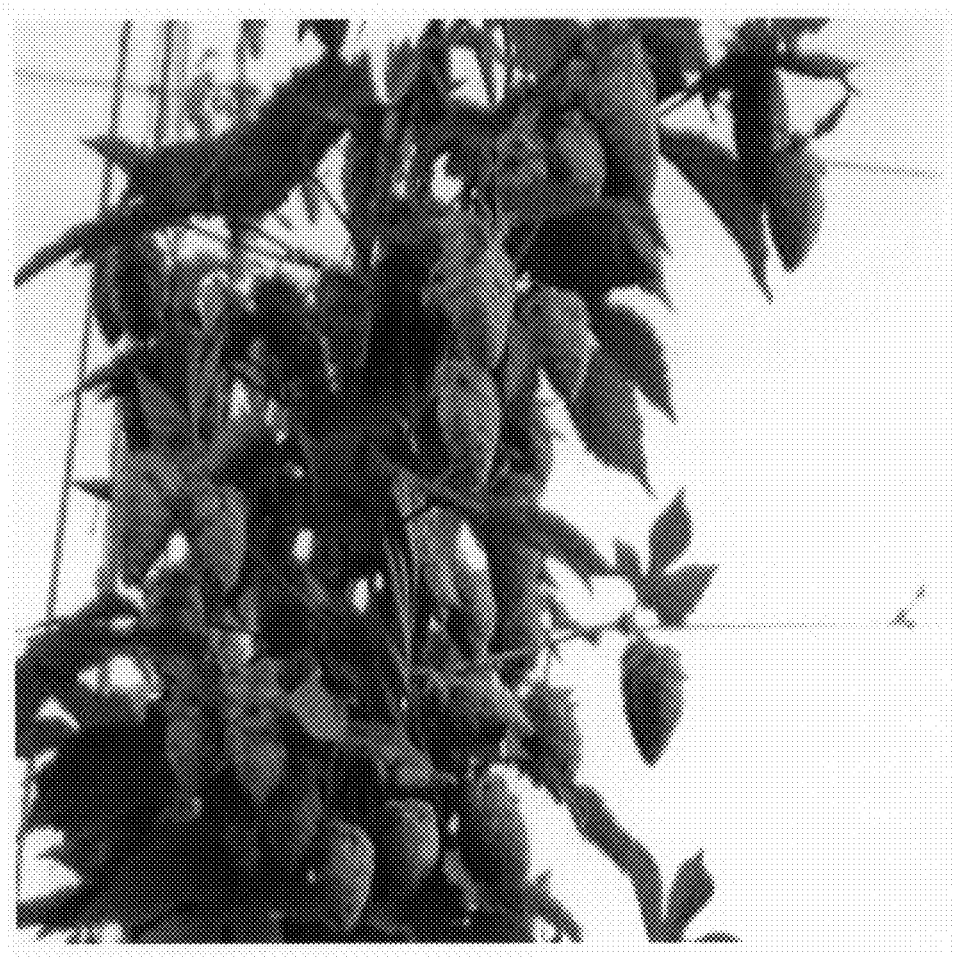
FIG. 2 illustrates a close up of whole cones and leaves of a 'HBC 637' hop plant as grown on the trellis.
Figure 3:
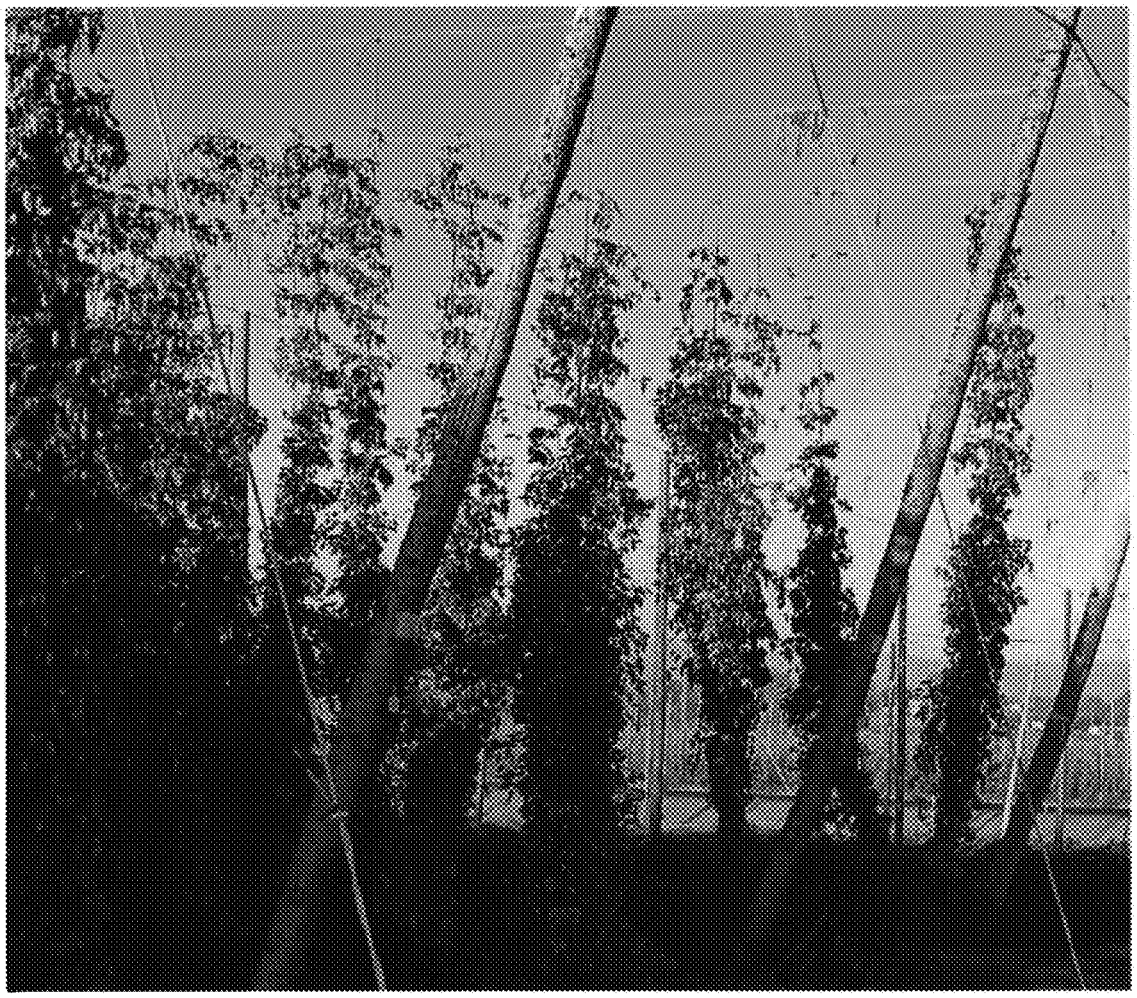
FIG. 3 illustrates a multiple of trellis with mature 'HBC 637' hop plants.

The colors of these illustrations may vary with lighting conditions and, therefore, color characteristics of this new variety should be determined with reference to the observations described herein, rather than from these illustrations alone.

COMPARISON OF 'HBC 637' TO PARENT PLANT AND COMPARISON CULTIVAR

Table 1. below, sets forth some of the distinguishing characteristics of 'HBC 637' as compared to its female parent 'HBC 366', and to the 'Chinook' cultivar as a closely comparable cultivar.

TABLE 1

| | INSTANT CV. 'HBC 637' | FEMALE PARENT 'HBC 366' | COMPARISON CV. 'CHINOOK' |
|---|---|---|---|
| Alpha (% of cone weight) | 13-15 | 14- 17 | 11.5-15 |
| Beta (% of cone weight) | 5.6-6.3 | 4.0-5.0 | 3.0-4.0 |
| Co-humulone (% of alpha acids) | 29-31 | 35-38 | 27-31 |
| Total Oil (mL/100 g) | 3.5-3.8 | 2.4-2.7 | 1.0-2.5 |
| Aroma Profile | Intense and complex notes of pine, floral, spice, citrus, | Apple, berry, lime, mango, melon, and | Grapefruit, spice, and pine. |

TABLE 1-continued

| | INSTANT CV. 'HBC 637' | FEMALE PARENT 'HBC 366' | COMPARISON CV. 'CHINOOK' |
|---|---|---|---|
| | and tropical aromas. | papaya. | |

DETAILED BOTANICAL DESCRIPTION

The following description is based on observations made during the 2014-2018 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. Color code designations are by reference to The R.H.S. Colour Chart, 4th ed., Copyright 2001, published by The Royal Horticultural Society of Great Britain.

Ploidy: Diploid.

Sex: Female.

Use: Brewing beer and ale.

Plant shape: Climbing Bine with Cylindrical Growth.

Time of flowering: Mid to Late July.

Harvest date: Typically harvested September 18 to September 25, but can deviate from this time period, depending on growing practices and location.

| Oil Analytical Characteristics (Averages): | |
|---|---|
| % Alpha Acid (% cone weight) | 13% to 15% |
| % Beta Acid (% cone weight) | 5.6% to 6.3% |
| % Cohumulone (% alpha acids) | 29% to 31% |
| Total Oil (ml/100 g of cones): | 3.5 ml to 3.8 ml Oil |

Bine:

*Bine color*.—Yellow-Green 144B.
*Stripe present*.—Yes.
*Stripe color*.—Red-Purple 60C.
*Stipule direction*.—Down.
*Stipule color*.—Yellow-Green 137A.
*Stipules per bine*.—38 to 74.
*Typical bine length*.—690 cm to 710 cm.
*Typical internode length on bine*.—20 cm to 26 cm.
*Bine diameter*.—11 mm at base; 10 mm at nine feet; and 9 mm at terminal end of eighteen feet.
*Average lateral length*.—76 cm to 112 cm.
*Typical internode length on lateral*.—3.5 cm to 21.0 cm.

Leaf:

*Arrangement*.—Opposite.
*Shape*.—Palmately Lobed.
*Apex*.—Aristulate.
*Pose*.—Down.
*Average length of mature leaf*.—17.5 cm to 18 cm.
*Average width of mature leaf*.—19.5 cm to 20 cm.
*Color of mature leaf upper surface*.—Yellow-Green 147A.
*Color of mature leaf lower surface*.—Yellow-Green 147A.
*Color of immature leaf upper surface*.—Yellow-Green 147A.
*Color of immature leaf lower surface*.—Yellow-Green 146A.
*Number of lobes*.—2 to 5.
*Margin*.—Serrate.
*Serrations per inch* (*typically*).—4 to 5.
*Petiole color at base*.—Yellow-Green 146D.
*Average petiole diameter* (*mature*).—2 mm to 4 mm.
*Average petiole length* (*mature, typical*).—10 cm to 12 cm.
*Venation*.—Palmate.
*Vein color*.—Yellow-Green 145C.
*Leaf blistering* (*on upper side of blade*).—Very Weak to Absent.

Cone:

*Avg. length*.—5.4 cm.
*Avg. diameter*.—1 cm.
*Bract tip color*.—Yellow-Green 145A.
*Bract tip position*.—Down.
*Bract base color*.—Yellow-Green 145C.
*Bracteole color*.—Yellow-Green 145C.
*Cone shape*.—Oblong.
*Bract shape*.—Orbicular.
*Bract tip shape*.—Cuspidate.
*Bract tip position*.—Recurved-Downward.
*Bract length*.—17.5 mm to 21 mm.
*Bract width*.—16 mm to 18 mm.
*Bract length of apex*.—2.2 mm on average.
*Degree of bract opening*.—Closed to Slightly Open.
*Bracteole shape*.—Ovate.
*Bracteole length*.—10.0 mm to 16 mm.
*Bracteole width*.—7.0 mm to 10 mm.
*Lupulin glands shape*.—Pedunculated Oblong Polyps.

The invention claimed is:

1. A new and distinct Hop plant as illustrated and described herein.

* * * * *